United States Patent [19]

Feaster

[11] Patent Number: 5,254,106
[45] Date of Patent: Oct. 19, 1993

[54] HYDRODISSECTION NEEDLE

[76] Inventor: Fred T. Feaster, 1125 College Ave., Fort Worth, Tex. 76104

[21] Appl. No.: 870,397

[22] Filed: Apr. 17, 1992

[51] Int. Cl.$^5$ ............................................. A61M 5/32
[52] U.S. Cl. ................................................ 604/272
[58] Field of Search ........................ 604/239, 272–274, 604/264; 606/107

[56] References Cited

U.S. PATENT DOCUMENTS

| | | | |
|---|---|---|---|
| 648,858 | 5/1900 | Dolge | 604/274 |
| 2,525,329 | 10/1950 | Wyzenbeek | 604/273 |
| 3,906,932 | 9/1975 | Ayres | 604/274 |
| 4,002,174 | 1/1977 | Reed et al. | 604/239 |
| 4,411,657 | 10/1983 | Galindo | 604/274 |

FOREIGN PATENT DOCUMENTS

| | | | |
|---|---|---|---|
| 0271775 | 6/1988 | European Pat. Off. | 604/239 |
| 0479474 | 8/1975 | U.S.S.R. | 604/239 |
| 1556656 | 4/1990 | U.S.S.R. | 604/272 |

*Primary Examiner*—John D. Yasko
*Assistant Examiner*—Anthony Gutowski
*Attorney, Agent, or Firm*—Arthur F. Zobal

[57] ABSTRACT

The hydrodissection needle has a sharp tip end and at least two elongated outlet openings which are located at or near the needle tip with their elongated axes extending rearward. In another embodiment, at least one elongated helical outlet opening is provided near the needle tip end.

8 Claims, 3 Drawing Sheets

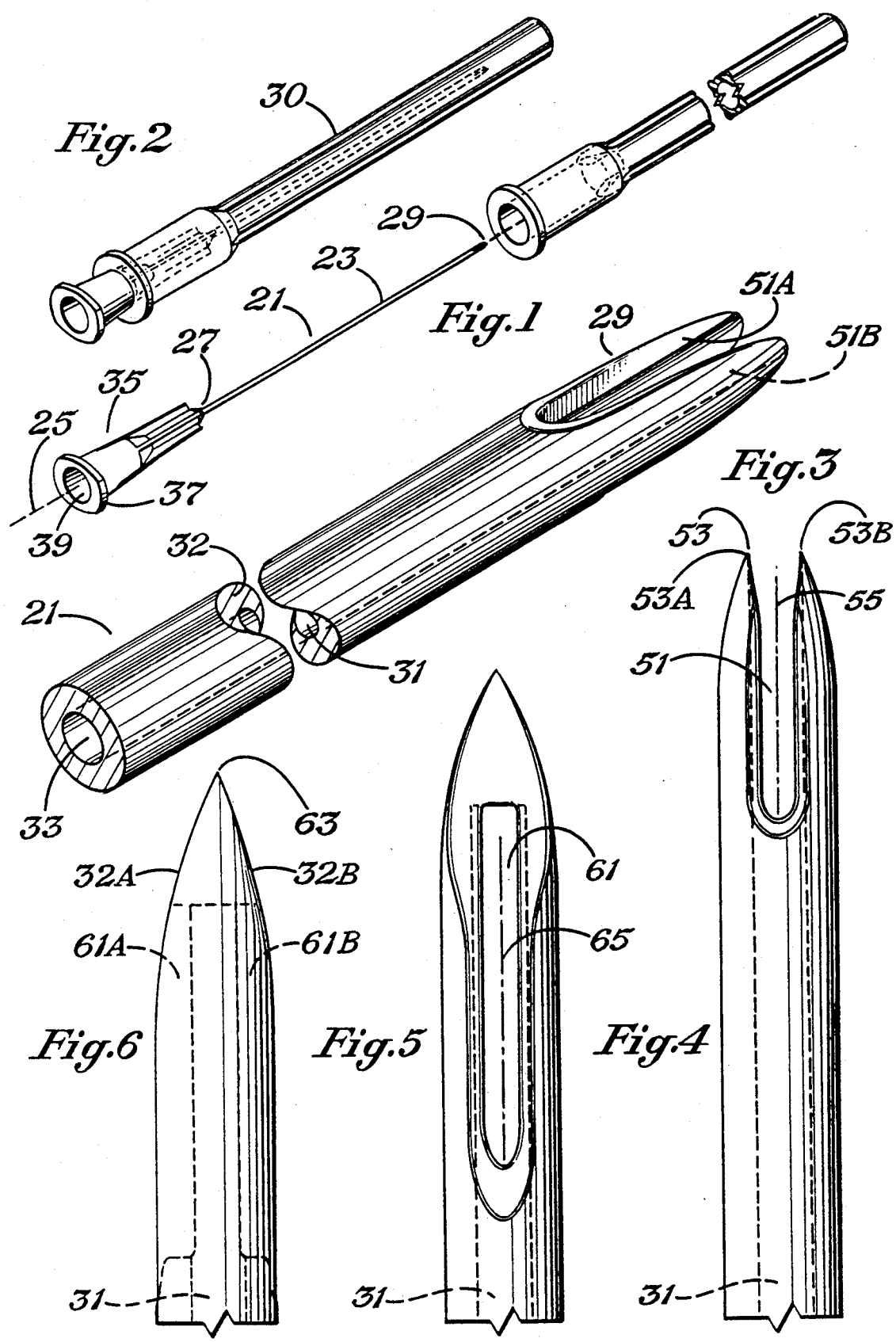

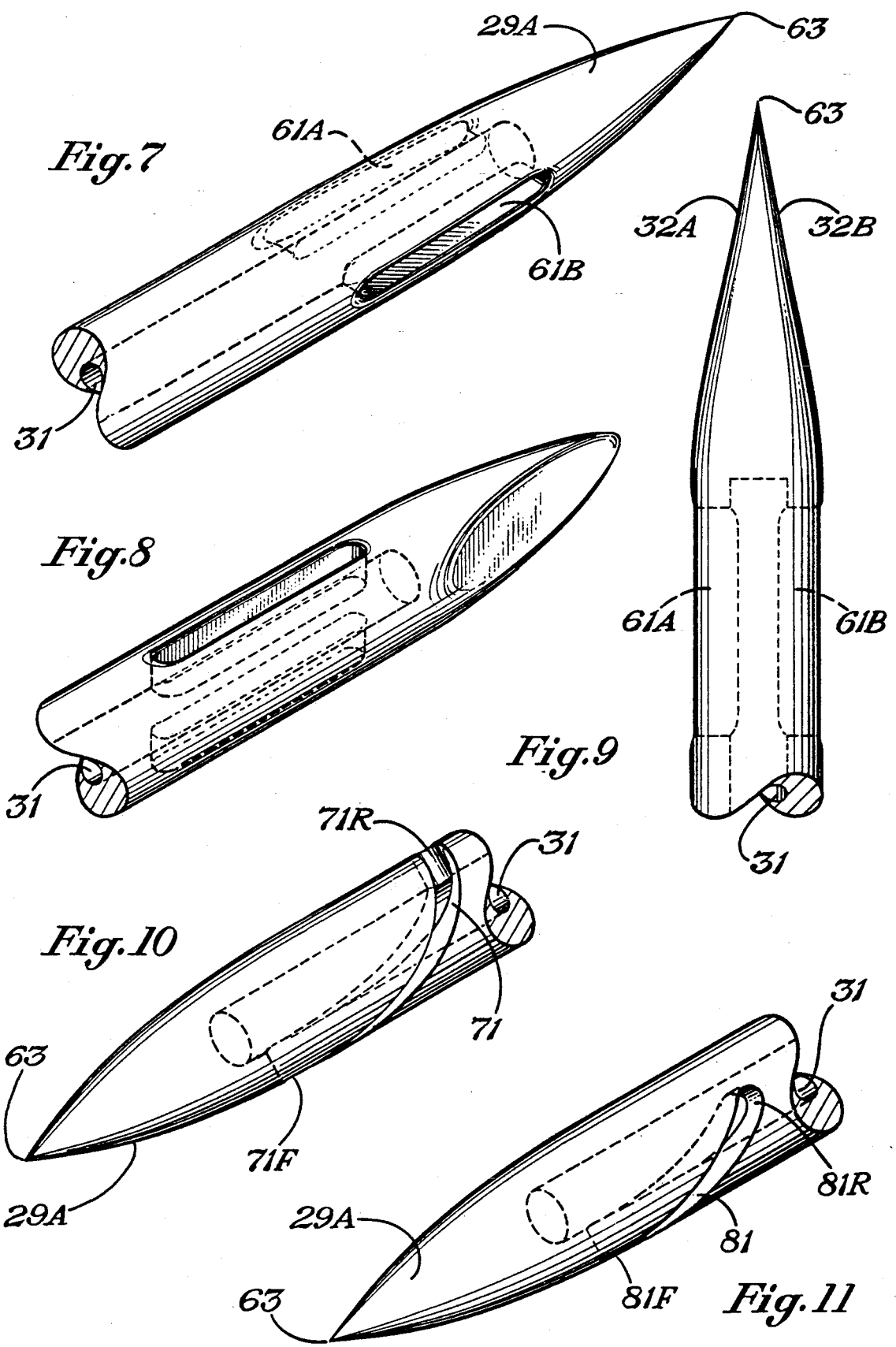

HYDRODISSECTION NEEDLE

BACKGROUND OF THE INVENTION

1. Field of the Invention

The invention relates to a needle for use in cataract extraction surgery of a persons eye.

2. Description of the Prior Art

In modern cataract extraction surgery, particularly phacoemulsification, one feature of the surgical technique is to separate and loosen the central nucleus from the surrounding cortex material. By loosening the nucleus, it increases accessibility for phacoemulsification by the phacoemulsifier. A common technique used for separating the central nucleus from the peripheral cortex is by means of hydrodissection, in which fluid, generally physiologic saline (balance salt) is forcibly injected through a needle which has been inserted into the lens material. When the needle tip has reached the proper anatomic level, within the lens, the fluid which has been injected through the needle under force from a syringe will seek, dissect and develop a natural cleavage plane between the hard central nucleus and the softer peripheral cortex. As fluid is further injected through the needle tip, the hydrodissection continues until the separation is complete. Critical to the success of this technique is the ability to place the needle tip in the proper anatomic location within the lens material. This depends on both the skill of the surgeon, and the ability of the needle to penetrate the lens material. It further relates to the adequate and proper functioning of the needle during fluid injection.

In general, there are 2 approaches for hydrodissection of the lens nucleus. One is an automated technique using a technology called Hydrosonics, in which a thin, hollow, mechanically driven, rapidly vibrating needle is introduced into the lens material. By virtue of the needle vibration, and injections of small increments of fluid through the needle, the needle penetrates into and separates the central nucleus from the peripheral epinucleus or cortex. This technique has the advantage of being capable of a very detailed and precise delineation of the central nucleus from the peripheral lens material. Additionally, because of its great penetrating capabilities, the vibrating needle can in fact, soften an otherwise hard central nucleus making it easier for phacoemulsification to be performed subsequently. Because it is automated, it is a technique that is somewhat easier to accomplish than using the manual techniques described below.

However, in view of the very adequate phacoemulsification machines available, the ability of the Hydrosonics technology to soften the central nucleus in addition to separating it from the peripheral cortex is possibly unnecessary, superfluous and somewhat "overkill" and represents capabilities which are beyond the usual need of the hydrodissection needle per se. Finally, the Hydrosonics technology has the disadvantage of being considerably more expensive than the manual techniques.

Manual techniques used for nucleus loosening and separation also involve a needle which is introduced into the lens material of the eye and through which fluid is injected, the fluid then separating the central nucleus from the peripheral cortex. The manual techniques, however, differ from the automated technique in that the needle is not vibrating or mechanically driven by automated technology in any way. The needle is simply introduced by hand by the surgeon passing the needle through the cataract incision and into the lens substance.

Various needles have been designed with different tip configurations to accomplish manual hydrodissection. One general basic design is that of a tapered blunt-tipped needle with a central opening at the end of the tip through which the fluid is injected. This design has the considerable disadvantage of introducing the irrigation port first as the leading part of the hydrodissection needle, directly into the lens material which allows for easy plugging of the irrigation port by the lens material as the needle progresses into the lens substance. Plugging of the irrigation port of the hydrodissection needle is a considerable disadvantage to the design which in fact may render the hydrodissection needle essentially non-functional due to the inability to irrigate fluid through the irrigation port. The needle may either be totally non-functional due to complete plugging by lens material in the irrigation port, or partially non-functional, the blockage being finally freed from the irrigation port when elevated irrigation pressure is applied, a situation which can be hazardous when performed with the needle tip inside the eye during surgery.

Another flaw in this particular design is that the tip itself is otherwise blunt and not as easily passed into the lens material as a sharp-tipped needle would be. A final flaw in this design is that fluid irrigation into the lens material occurs only at one anatomic level, that being the level of the single irrigation port at any given time. This limitation of irrigation to the anatomic location of a single irrigation port requires considerably greater precision in proper placement of that irrigation port within the lens material making the procedure much more difficult requiring an undesirable degree of accuracy in placement of the needle tip.

Other needles have been designed in the past which, while not being designed specifically for hydrodissection would alleviate some but not all of the afore mentioned design flaws of: 1) end on location of the irrigation port; 2) limitation to a single irrigation port; 3) blunt-tipped needle.

One hydrodissection needle, converts the generally round configuration of the afore mentioned hydrodissection needle to a flat configuration which would allow easier passage through the lens substance. This design, however, continues to have the problems with end on irrigation which is limited to a single port with a blunt tip. An additional design, the Bishop-Harmon anterior chamber needle, converts the end on irrigation port to an oval configuration which conceivably would give a slightly broader irrigation range to the sides. Another needle possesses a sharp tip, but still with an end opening.

Needles with multiple irrigating ports have also been utilized, with the location of the irrigating ports occupying simultaneously the end of the needle, and the side needle shaft. This particular design, however, has the difficulty of having a blunt end.

Attempts to solve the difficulties of blunt-end have been addressed in the Shahinian lacrimal cannula, this cannula actually being used for irrigation of the nasal lacrimal tear duct system and not for hydrodissection. It does have the features of a modestly pointed tip with the irrigating port located behind the tip. An additional needle which is actually used for suturing, is the Simco suturing needle which has a sharp point, and end-on irrigation port and a second port which conceivably could be used for irrigation located somewhat behind the tip.

Many other needles have also been designed with an irrigation port located proximal to the distal cannula or needle tip. These various alterations, have not been sharp or in any way configured to allow introduction into the lens material.

Finally, additional "needle" or cannula designs have incorporated double cannulas with an irrigating port located on one needle which is immediately adjacent to a second needle which has an additional irrigation port. Again, these needles are not designed for hydrodissection in that they do not have a sharp tip and the double cannula configuration is extremely bulky and unusable for hydrodissection.

Thus the prior art afore mentioned needles and cannulas, have design flaws namely being: 1) end-on location of the port; 2) presence of a single irrigating port; 3) blunt tip; 4) irrigation port configuration limited to a round or flattened hole at or near the end of the hydrodissection needle.

SUMMARY OF THE INVENTION

It is an object of the invention to provide a hydrodissection needle which eliminates or minimizes the problems of the prior art needles.

The hydrodissection needle of the invention in one embodiment has a sharp tip end and at least two straight elongated outlet openings which are located at or near the needle tip with their elongated axes extending rearward. In another embodiment, at least one elongated helical outlet opening is provided near the needle tip.

The outlet openings of the hydrodissection needle of the invention improves irrigation capabilities; decreases the possibility of port plugging by lens material; and eliminates the need for extremely precise tip location in the eye to accomplish the proper irrigation location site for hydrodissection. By providing the needle with a sharp pointed front end configuration, the ability to pass the needle into the lens material is enhanced. Thus use of the needle of the invention facilitates hydrodissection.

BRIEF DESCRIPTION OF THE DRAWINGS

FIG. 1 illustrates a hydrodissection needle and a protective shield.

FIG. 2 illustrates the hydrodissection needle of FIG. 1 located in a protective shield.

FIG. 3 is an enlarged isometric view of the tip end of one embodiment of a hydrodissection of the invention.

FIG. 4 is a side view of the tip end of the needle of FIG. 3 showing a plan view of the outlet opening.

FIG. 5 is a side view of the tip end of another embodiment of the needle of the invention showing a plan view of the outlet opening.

FIG. 6 is a side view of the tip end of the needle of FIG. 5 rotated ninety degrees relative to the position of the needle in FIG. 5.

FIG. 7 is an isometric view of the tip end of another embodiment of the needle of the invention.

FIG. 8 is an isometric view of the tip end of another embodiment of the needle of the invention.

FIG. 9 is a side view of the tip end of the needle of FIG. 8 illustrating the outlet openings in dotted lines located 90 degrees relative to those of FIG. 8.

FIG. 10 is an isometric view of the tip end of another embodiment of the needle of the invention.

FIG. 11 is an isometric view of the tip end of another embodiment of the needle of the invention.

DESCRIPTION OF THE PREFERRED EMBODIMENT

Figure 12:
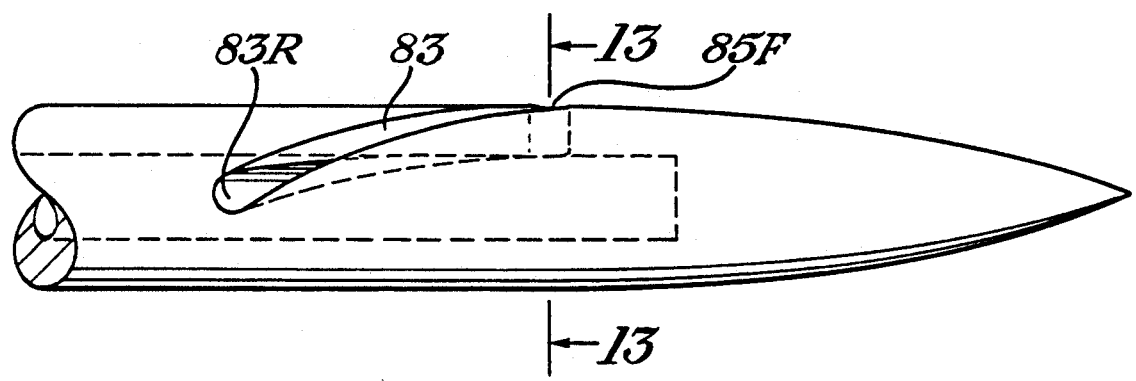
FIG. 12 is a side view of the tip end of the needle of FIG. 11 as seen from the side opposite that of FIG. 11.

Referring now to FIGS. 1 and 2, there is illustrated a hydrodissection needle 21 comprising an elongated cylindrical shaped member 23 having a central axis 25 along its length, a rear end 27 and a sharp pointed front end 29. Reference numeral 30 identifies a protective shield into which the needle is inserted when not in use. In FIGS. 3–11 the needle 21 is the same except for the shape of the front end and the outlet port at the front end. Referring also to FIG. 3, the needle 21 also has a central aperture 31 extending generally along the axis 25 of the member 23 from the rear end 27 to a position at or near its front end 29. A rear inlet opening 33 leads to the central aperture 31. A rear member 35 having a flanged rear end 37 and an opening 39 extending therethrough is attached to the rear end 27 of the member 23 with the opening 39 being in fluid communication with the central aperture 31. The member 35 allows a syringe to be coupled thereto by way of the flange 37 to allow irrigation fluid (liquid) to be injected through the needle 21 by way of the opening 39 the inlet opening 33, central aperture 31 and the outlet port at the front end 29.

Reference now will be made to FIGS. 3–11 for the different embodiments of the outlet ports of the needle of the invention. Referring first to FIG. 4, the outlet port comprises an elongated aperture or opening 51 extending through the member 23 from the tip end 53 rearward. The aperture 51 extends through opposite sides of the wall 32 of the member 23 thus defining two openings 51A and 51B formed through opposite sides of the wall 32 which are in fluid communication with the central aperture 31. The elongated axes 55 of the openings 51A and 51B are parallel with the central axes 25. The tip end 53 comprises two sharp tip members 53A and 53B.

Referring to FIGS. 5 and 6, the front end outlet port comprises an elongated aperture 61 extending through the member 23 from near the tip end 63 rearward. The aperture 61 extends through opposite sides of the wall 32 of the member 23 thus defining two openings 61A and 61B formed through opposite sides of the wall 32 which are in fluid communication with the central aperture 31. The elongated axes 65 of the openings 61A and 61B are parallel with the central axes 25. The front wall sides 32A and 32B of the member 23 through which the openings partially 61A and 61B extend are flattened and the tip end 63 is sharp and pointed.

The needle front end outlet port of FIG. 7 is similar to that of FIGS. 5 and 6 except that the front end portion 29A forward of the openings 61A and 61B is conical shaped and the tip end 63 is sharp and pointed.

The needle front end outlet port of FIGS. 8 and 9 is the same as that of FIGS. 5 and 6 except that the openings 61A and 61B are more rearward of the tip end 63 and in FIG. 8, are located 90 degrees relative to those of FIGS. 5 and 6..

Referring to FIG. 10, the front end outlet port of the member 23 comprises an elongated helical shaped opening 71 extending through the wall 32 one hundred eighty (180) degrees around the member 23 from a front position 71F to a rear position 71R and in fluid communication with the central aperture 31 over the entire 180 degrees. The front position 29A of the needle forward of the opening 71 is conical shaped and the tip end 63 is sharp and pointed.

Figure 13:
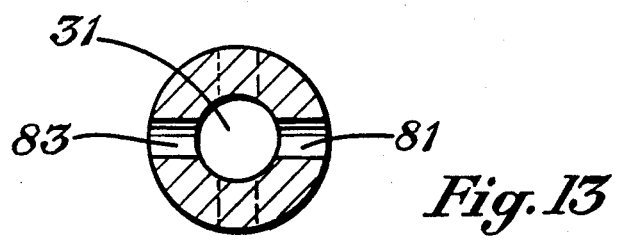
FIG. 13 is a cross-section of the needle of FIG. 11 taken along the lines 13—13 thereof and rotated 90 degrees.

Referring to FIGS. 11-13, the front end outlet port of the member 23 comprises two elongated helical shaped openings 81 and 83 each extending through the wall 32 ninety (90) degrees around the member from front positions 81F and 83F to rearward positions 81R and 83R respectively and in fluid communication with the central aperture 31 over their entire 90 degrees. The front ends of the openings 81 and 83 are located 180 degrees apart and the rear ends 81 and 83 are located 180 degrees apart. The front end portion 29A of the needle is conical shaped and the tip end 63 is sharp and pointed.

Thus the outlet openings of the needles of the invention, are elongated and slit-like thereby increasing the area of the irrigation port; decreasing the possibility of port plugging by lens material; and eliminating the need for extremely precise tip location to accomplish the proper irrigation located site for hydrodissection. By making the injection port slit-like the possibility for multiple locations for injection is greater and the strategic location of these slit-like irrigation ports allows hydrodissection to be considerably facilitated. In addition to increasing the irrigation area, the sharp configuration of the needle will maximize the ability of the needle to be passed into the lens material.

In one embodiment, the needle member 23 is formed of stainless steel and has a length of ½-1½ inches, an outside diameter of 23 or 25 gauge, and an inside diameter defining its central aperture 31 of standard size. The outlet openings 51 and 61 may have a length of ½-3 or 4 mm and a width of approximately 0.2-0.3 mm. The length of the opening 71 may be ½-3 or 4 mm and its width 0.2-0.3 mm. The length of each of the openings 81 and 83 may be ½-3 mm and their widths 0.2-0.3 mm.

What is claimed is:

1. A hydrodissection needle for use for performing surgery on a person's eye, comprising:
    an elongated member having a central axis extending along its length, a rear end, an elongated body portion, and a sharp front end with two flattened opposite facing sides extending rearward from said sharp front end to said elongated body portion,
    said two flattened sides being the only flattened sides extending rearward from said sharp front end and being free of apertures,
    a central aperture extending generally along said central axis of said member from said rear end to a position near said front end,
    said member having a side wall surrounding said central aperture,
    said elongated body portion being generally cylindrical having the same outside diameter from the rear of said flattened sides along a substantial portion of the length of said elongated body portion,
    said member having a rear inlet opening leading to said central aperture at said rear end, and
    at least one outlet opening formed through said elongated body portion near and rearward of said two flattened sides and in fluid communication with said central aperture for allowing the flow of liquid through said member from said rear inlet opening at said rear end, by way of said central aperture and from said central aperture outward by way of said outlet opening.

2. The hydrodissection needle of claim 1, wherein said outlet opening is elongated and has an elongated axis generally parallel to said central axis of said member.

3. The hydrodissection needle of claim 1 comprising a second outlet opening formed through said elongated body portion near and rearward of said two flattened sides,
    said second outlet opening being formed through said elongated body portion on a side opposite the side of which said one outlet opening is formed.

4. The hydrodissection needle of claim 3 wherein said two outlet openings are elongated and have elongated axes respectively generally parallel to said central axis of said member.

5. The hydrodissection needle of claim 1, wherein:
    said two flattened sides define two planes respectively which extend rearward from said sharp end and define an acute angle,
    said outlet opening is located between rearward extensions of said two planes in a central plane that extends through said axis and bisects said acute angle.

6. The hydrodissection needle of claim 5 wherein said outlet opening is elongated and has an elongated axis generally parallel to said central axis of said member.

7. The hydrodissection needle of claim 5 comprising a second outlet opening formed through said elongated body portion near and rearward of said two flattened sides,
    said second outlet opening being located between rearward extensions of said two planes,
    said second outlet opening being formed through said elongated body portion on a side opposite the side on which said one outlet opening is formed and being located in said central plane.

8. The hydrodissection needle of claim 7, wherein said two outlet openings are elongated and have elongated axes respectively generally parallel to said central axis.

* * * * *